US010874516B2

(12) United States Patent
Jagger et al.

(10) Patent No.: US 10,874,516 B2
(45) Date of Patent: Dec. 29, 2020

(54) IMPLANTABLE PENILE PROSTHESES

(71) Applicant: Boston Scientific Scimed, Inc., Maple Grove, MN (US)

(72) Inventors: Karl Jagger, Minnetonka, MN (US); Brian Watschke, Minnetonka, MN (US); Steven Brncic, Minnetonka, MN (US); David Booth, Minnetonka, MN (US); William Furniss, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 585 days.

(21) Appl. No.: 15/321,092

(22) PCT Filed: Jun. 26, 2015

(86) PCT No.: PCT/US2015/037964
§ 371 (c)(1),
(2) Date: Dec. 21, 2016

(87) PCT Pub. No.: WO2015/200784
PCT Pub. Date: Dec. 30, 2015

(65) Prior Publication Data
US 2017/0165071 A1 Jun. 15, 2017

Related U.S. Application Data

(60) Provisional application No. 62/018,191, filed on Jun. 27, 2014.

(51) Int. Cl.
*A61F 2/26* (2006.01)
*A61F 2/48* (2006.01)

(52) U.S. Cl.
CPC .......... *A61F 2/26* (2013.01); *A61F 2002/484* (2013.01); *A61F 2250/0003* (2013.01)

(58) Field of Classification Search
CPC ....................................................... A61F 2/26
(Continued)

(56) References Cited

U.S. PATENT DOCUMENTS 4,545,081 A 10/1985 Nestor et al.
4,590,927 A * 5/1986 Porter ..................... A61F 2/26
600/40

(Continued)

FOREIGN PATENT DOCUMENTS

WO 2015200784 A3 12/2015

OTHER PUBLICATIONS

International Preliminary Report for PCT Application No. PCT/US2015/037964, dated Jan. 5, 2017, 8 pages.
(Continued)

*Primary Examiner* — Samuel G Gilbert
(74) *Attorney, Agent, or Firm* — Brake Hughes Bellermann LLP

(57) ABSTRACT

A penile prosthesis system including at least one cylinder that has an elongated inner opening, a cylinder spring positioned within the opening and adjacent to a distal end of the inner opening, an activation plunger positioned within a proximal end of the opening of the cylinder, and a plurality of discrete members within the inner opening between the cylinder spring and the plunger. The system further includes a pump comprising a spring and a tube connected to and extending from the cylinder and the pump, wherein the tube is configured for transferring fluid to the at least one cylinder upon activation of the pump.

16 Claims, 2 Drawing Sheets

(58) Field of Classification Search
USPC .......................................................... 600/40
See application file for complete search history.

(56) References Cited

U.S. PATENT DOCUMENTS

| | | | |
|---|---|---|---|
| 4,693,739 A | 9/1987 | Manabe et al. | |
| 4,875,472 A | 10/1989 | Levius et al. | |
| 5,437,605 A | 8/1995 | Helmy et al. | |
| 2005/0014993 A1* | 1/2005 | Mische | A61F 2/26 600/40 |
| 2011/0201875 A1* | 8/2011 | Stroumpoulis | A61F 5/005 600/37 |
| 2013/0190559 A1* | 7/2013 | Little | A61F 2/26 600/40 |
| 2014/0051920 A1 | 2/2014 | Vaingast et al. | |

OTHER PUBLICATIONS

International Search Report and Written Opinion for PCT Application No. PCT/US2015/037964, dated Jan. 15, 2016, 15 pages.

\* cited by examiner

IMPLANTABLE PENILE PROSTHESES

PRIORITY CLAIM TO PROVISIONAL APPLICATION

This application claims priority to U.S. Provisional Patent Application No. 62/018,191, filed Jun. 27, 2014, the entire contents of which are incorporated herein by reference in its entirety.

TECHNICAL FIELD

The present invention relates to systems for treating erectile dysfunction and other urological disorders. In particular, the invention relates to implantable penile prostheses.

BACKGROUND

A common treatment for erectile dysfunction includes the use of a penile implant device. One type of penile implant device includes a pair of cylinders, each of which includes a malleable member that provides sufficient friction and rigidity for the patient to configure the device for concealment or for intercourse.

Another type of penile implant device includes a pair of cylindrical prostheses that are implanted into the corpus cavernosum of the penis. In some instances, the prostheses are inflatable and are connected to a fluid-filled reservoir through a pump and valve assembly. This type of system is commonly referred to as a three-piece implantable penile prosthesis. With these systems, there is typically one tube extending from each of the two cylindrical prostheses and connecting to the pump, and one tube connecting the pump to the reservoir. The pump is typically implanted into the scrotum of the patient, and the reservoir is implanted in the abdomen. To activate the penile implant device, the patient actuates the pump using one of a variety of methods that cause fluid to be transferred from the reservoir through the pump and into the prostheses. This results in the inflation of the prostheses and produces rigidity for a normal erection. Then, when the patient desires to deflate the prostheses, a valve assembly within the pump is actuated in a manner such that the fluid in the prostheses is released back into the reservoir. This deflation returns the penis to a flaccid state.

Another type of system that can be used is commonly referred to as a two-piece system, which differs from the three-piece system in that it does not include a separate reservoir. Rather, the pump in some two-piece systems also functions as the reservoir. The pump of this type of system is typically directly connected to the cylinders implanted in the corpus cavernosum of the penis. These systems are often relatively basic in their operation, and involve steps such as repeatedly squeezing and releasing the pump to transfer fluid to the cylinders, where the pump can be squeezed as many times as necessary to achieve the desired firmness of the cylinders. Depending on the system, this can take a significant period of time and may require more repetitive squeezing and releasing cycles than is desirable or convenient for the user.

While the use of three-piece systems is common and generally provides acceptable performance results, the implantation of the three distinct parts of the system in different parts of the body is typically more invasive to the patient than a system that requires accessing fewer areas of the body. Further, due to the positioning of the pieces of the system relative to each other and the type of pumping mechanism provided with the system, some two and three-piece systems require relatively significant manipulation by the user to transfer fluid from the reservoir. Such manipulation may be either time-consuming or difficult, particularly for users who have problems with dexterity or complicated instructions. Thus, it is desirable to provide an implantable prosthetic penile device or system that feels natural to the user, is easy to activate and deactivate, and that has a relatively long life cycle even after repeated activations and deactivations of the system.

It is also desirable to provide an implantable prosthetic penile device or system in which the state of the implant can be changed from flaccid to rigid with minimal fluid transfer. For example, a system that can provide for an erection with approximately one-tenth of the volume of fluid transfer into and out of the cylinders as compared to current systems would further advance the performance of such devices in the market.

SUMMARY

In one aspect of the invention, a penile prosthesis system is provided, which includes at least one cylinder. The cylinder includes an elongated inner opening, a rod positioned within the inner opening and extending along at least a portion of a length of the cylinder, a plurality of articulating segments operatively connected to the rod and spaced along a length of the rod, and an activation plunger operatively connected to a proximal end of the rod within the inner opening of the cylinder. The system further includes a pump comprising a spring and a tube connected to and extending from the cylinder and the pump, wherein the tube is configured for transferring fluid to the at least one cylinder upon activation of the pump.

In another aspect of the invention, an implantable cylindrical member is provided for erectile dysfunction, the cylindrical member including a first elongated tubular member comprising an inner diameter, an outer surface, and a plurality of slits spaced longitudinally from each other along a length of the first tubular member, wherein each of the slits has first and second ends and extends around a portion of a circumference of the first tubular member, and wherein the first and second ends of adjacent slits are offset relative to each other along the length. The cylindrical member further includes a second elongated tubular member at least partially positionable within the first tubular member, the second tubular member having an outer diameter that is smaller than the inner diameter of the first tubular member, and a plurality of slits spaced from each other along a length of the second tubular member, wherein the first and second tubular members are repositionable relative to each other to vary the rigidity of the implantable cylindrical member.

In another aspect of the invention, a penile prosthesis system is provided that includes at least one cylinder having an elongated inner opening, a cylinder spring positioned within the opening and adjacent to a distal end of the inner opening, an activation plunger positioned within a proximal end of the opening of the cylinder, and a plurality of discrete members within the inner opening between the cylinder spring and the plunger. The system further includes a pump comprising a spring, and a tube connected to and extending from the cylinder and the pump, wherein the tube is configured for transferring fluid to the at least one cylinder upon activation of the pump. The tube also allows for the return of fluid to a fluid storage area after depressurization of the cylinders.

In aspects of the invention described herein, the penile prosthesis systems can alternatively or additionally include an integrated inflation system for transferring fluid to the cylinders. Such a system may include an electronic pump with remote activation thereof. For example, the system can include a piezoelectric pump for drawing fluid from a reservoir and moving the fluid to the cylinder(s). The piezoelectric pump can be wirelessly activated to control the inflation and/or deflation of the cylinder(s). For another example, the systems may include an electric pump, an implant controller, and an implantable power supply that provides power to the pump.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
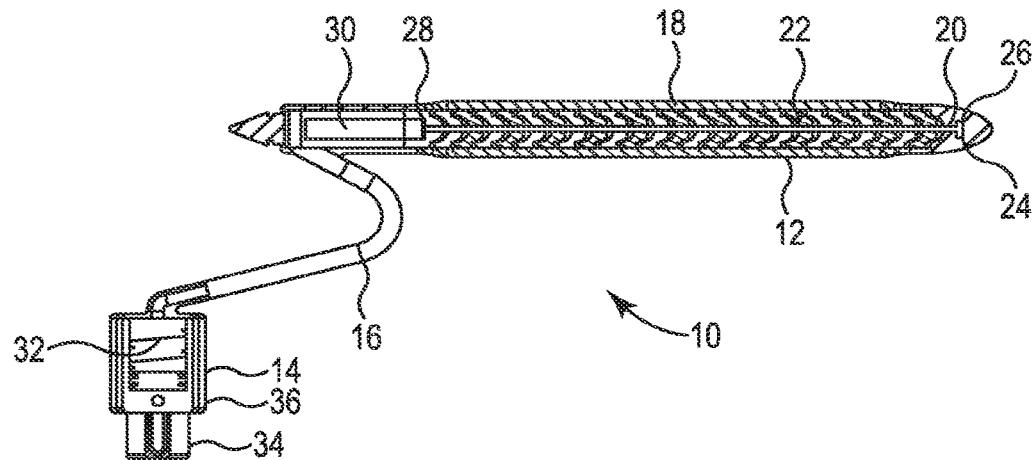
FIG. 1 is a front, partial cross-sectional view of an embodiment of a penile prosthesis system of the invention.

Referring now to the Figures, wherein the components are labeled with like numerals throughout the several Figures, and initially to FIG. 1, an embodiment of an implantable penile prosthesis system 10 is illustrated, according to the invention. Penile prosthesis system 10 includes at least one expandable cylinder 12 connected to a pump 14 by a tube 16. In general, when the penile prosthesis system 10 is implanted into a person, the pump 14 is positioned within the person's scrotum, one or more expandable cylinders 12 are positioned within the person's corpus cavernosum, and the tube 16 will extend between these components. While only one cylinder 12 and tube 16 are shown in FIG. 1, the system 10 may include an additional cylinder 12 and corresponding tube 16 that is attached to the pump 14. Each cylinder 12 can be relatively flexible for comfort and conformability within a patient, and may have a constant or varying (e.g., tapered) diameter along its length.

Cylinder 12 includes an outer shell 18 that encloses and protects the inner components of the cylinder. Cylinder 12 further includes a central rod 20 that extends generally along its longitudinal axis. Multiple articulating segments 22 are operatively connected to and positioned along the length of the central rod 20. Central rod 20 further includes a distal end 24 that can optionally terminate at a T-shaped member 26, and a proximal end 28 in communication with an activation plunger 30.

Pump 14 includes a spring 32 and a sliding member 34 that is slideable relative to a housing 36 in which spring 32 is positioned. The sliding member 34 can be grasped and pressed in order to compress the spring 32, after which the sliding member 34 is temporarily lockable into place until it is desired to release the spring 32. In operation, this pressing of the sliding member 34 toward the housing 36 will compress the spring 32 and move fluid within the system 10 through the tube 16 and toward the activation plunger 30. The change in pressure will move the activation plunger 30 in a distal direction and drive the articulating segments 22 toward the distal end of the cylinder 12, which changes their condition to be "locked" and also makes the cylinder 12 at least somewhat more rigid. The length of the cylinder 12 may also increase when the articulating segments 22 are moved to their "locked" state. In order to release the articulating segments 22 and return the cylinder 12 to its "unlocked" or more flexible state, the sliding member 34 is released relative to the housing 36 so that the bias of the spring 32 forces the sliding member 34 back toward its original position.

In embodiments of the invention, girth increase can also be achieved. In one example, a portion of the transferred fluid may be directed or shunted to a space between the inner and outer walls, thereby inflating or expanding the device circumferentially. In another example, girth can be increased by providing articulating segments made of a material that deforms outwardly when compressed along a longitudinal axis, particularly when the length is contained or limited.

In this embodiment of the invention, it is therefore possible for a single action by the user (i.e., moving the sliding member 34 toward the housing 36 to compress the spring 32 by a certain amount) to change the cylinder 12 from a relatively flexible state to a more rigid state. The volume of fluid needed in the system to cause this activation is relatively small.

Figure 2:
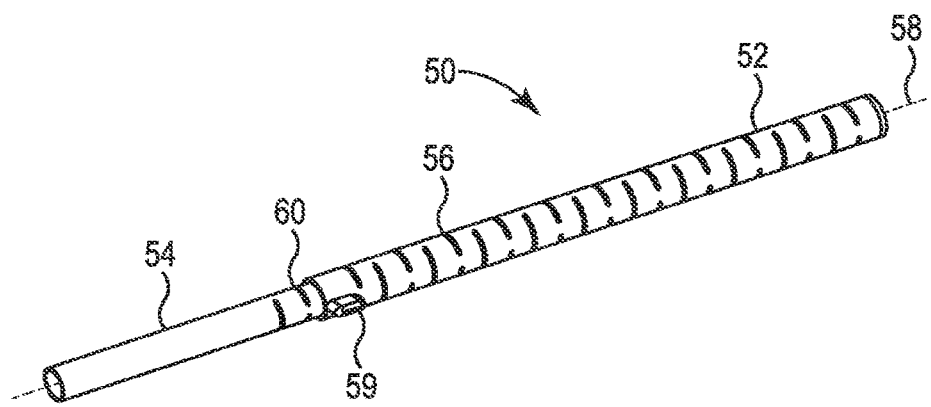
FIG. 2 is a perspective view of an embodiment of a penile prosthesis system of the invention.

FIG. 2 illustrates another embodiment of a portion of a penile prosthesis system. In particular, a penile prosthesis 50 includes an outer tubular member 52 in which an inner tubular member 54 is positioned along at least a portion of its length. Outer tubular member 52 is an elongated, cylindrical shaped member that is positionable within the person's corpus carverosae. Outer tubular member 52 comprises an outer cylindrical shaped wall through which multiple slits 56 are cut. As shown, the slits 56 are generally oriented in a perpendicular direction to a longitudinal axis 58 of the penile prosthesis 50, and are spaced from each other along at least a portion of its length. It is contemplated, however, that the slits are arranged at an angle to the longitudinal axis 58 that is not perpendicular. Each of the slits 56 generally extends only around a portion of the perimeter of the tubular member 52 in a pattern such that the ends of the slits are offset relative to each other along the length of the tubular member 52. Outer tubular member 52 can further include an extending tab 59 at its proximal end. This tab 59 can be used to manipulate the tubes 52, 54 relative to each other as will be described below.

Inner tubular member 54 has an outer diameter that is smaller than the inner diameter of the outer tubular member 52 so that it can be moved relative to the inner tubular member in a telescoping and/or rotational manner. Similar to the description of the outer tubular member 52 set out above, inner tubular member 54 is an elongated, cylindrical shaped member that includes an outer cylindrical shaped wall through which multiple slits 60 are cut. As shown, the slits 60 are generally oriented in a perpendicular direction to the longitudinal axis 58 of the penile prosthesis 50 (although they can instead be differently oriented), and are spaced from each other along at least a portion of its length. Each of the slits 60 generally extends only around a portion of the perimeter of the inner tubular member 54 in a pattern such that the ends of the slits are offset relative to each other along the length of the tubular member 54. In an aspect of the invention, the slits 60 are spaced at the same or a similar distance from each other as the distance that the slits 56 are spaced from each other, although it is contemplated that the slits of the two tubular members are spaced at different distances from each other.

Penile prosthesis 50 is changeable from a flaccid state to a more rigid state by rotating the inner and outer tubular members relative to each other to align and misalign the slits 56 and 60, or by linear translation of the inner and/or outer tubular members. For one example, in order to place the penile prosthesis 50 in a relatively flaccid or flexible state, the inner and outer tubular members 52, 54 are rotated relative to each other by gripping the outer tubular member 52 and rotating it in either direction until their respective slits 56, 60 are sufficiently aligned with each other so that a desired flaccidity is reached. In another example, to place the penile prosthesis 50 in a relatively rigid state, the inner and outer tubular member 52, 54 are rotated relative to each other until their respective slits 56, 60 are sufficiently misaligned with each other so that a desired rigidity is reached. The rotation can be aided by the use of the extending tab 59 that can provide tactile information to the user regarding the rotational orientation of the outer tubular member 52.

In another aspect of the invention, the outer tubular member 52 and inner tubular member 54 can be provided with a matched set of ramps or cams in their construction. In this way, pulling the outer tubular member 52 relative to the inner tubular member 54 will cause the tubular members to rotate relative to each other to cause alignment and misalignment of the slits 56 relative to the slits 60, as desired.

The tubular member 50 may be made of a thin-walled stainless steel or NiTi material that is reconfigurable as described above. The characteristics of the slits for a particular tubular member, including the number, spacing, length, etc. of the slits, can be selected to provide specific desired characteristics to the tubular member when manipulated in particular ways. The slits can be laser cut into the tubular member, or can be provided using another type of tool and/or operation. For example, the slits can be molded into the length of the tubular member 50. In any case, the slits can be simple cuts in the tubular member that do not involve removal of material from the tubular member, or can alternatively be formed more as "notches" in which material from the tubular member is removed to create gaps along the length of the tubular member.

Figure 3:
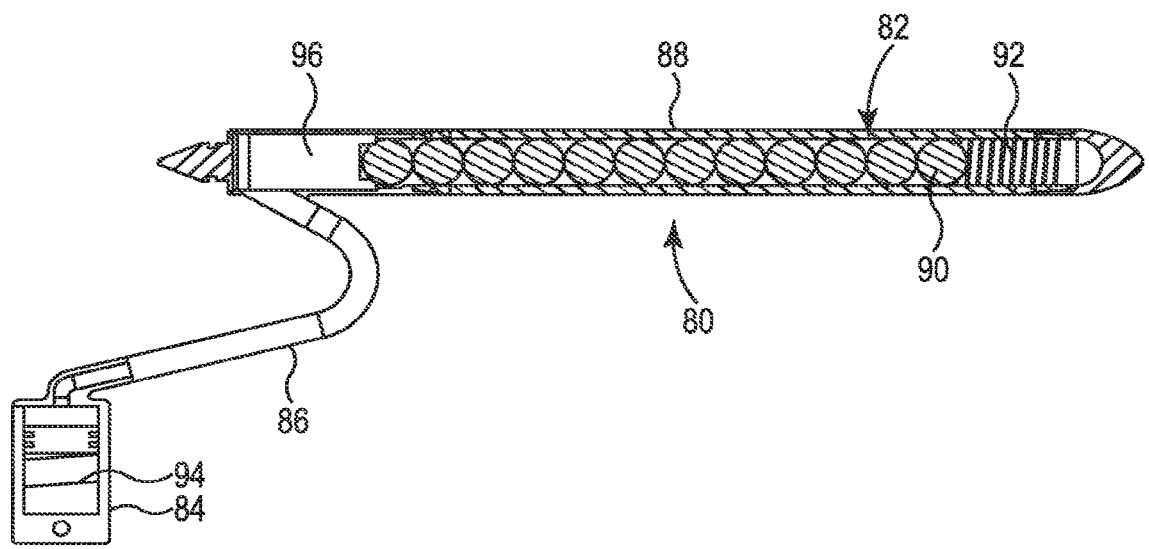
FIG. 3 is a front, partial cross-sectional view of an embodiment of a penile prosthesis system of the invention.

FIG. 3 illustrates an embodiment of an implantable penile prosthesis system 80, according to the invention. Penile prosthesis system 80 includes at least one elongated cylinder 82 connected to a pump 84 by a tube 86. In general, when the penile prosthesis system 80 is implanted into a person, the pump 84 is positioned within the person's scrotum, one or more expandable cylinders 82 are positioned within the person's corpus cavernosum, and the tube 86 will extend between these components. While only one cylinder 82 and tube 86 are shown in FIG. 3, the system 80 may include an additional cylinder 82 and corresponding tube 86 that is attached to the actuation member 84. Each cylinder 82 can be relatively flexible for comfort and conformability within a patient, and may have a constant or varying (e.g., tapered) diameter along its length.

Cylinder 82 includes an outer shell 88 that encloses and protects the inner components of the cylinder. Cylinder 82 further includes multiple spheres 90 positioned along its length. A cylinder spring 92 is positioned within the outer shell 88 adjacent to the distal end of the cylinder 82. With this embodiment, the material that surrounds the spheres 90 within the cylinder 82 is distensible and can be driven down around the spheres 90 to "lock" them with minimal fluid volume transfer and low pressure (e.g., less than 2 ATM) by having it paired with a non-distensible outer member. It is understood that the spheres 90 may be the same or different sizes along the length of the cylinder 82 and/or that the cylinder 82 includes multiple members that have a shape that is different from spherical, such as elliptical, oval, tubular, and the like.

Pump 84 includes an activation spring 94, and can further include an activation mechanism that is used to compress the activation spring 94 and optionally lock it in place. In operation, activating the pump 84 will involve compression of the spring 94 and movement of fluid within the system 80 through the tube 86 and toward a plunger 96 located at the distal end of the cylinder 82. The change in pressure will move the plunger 96 in a distal direction and drive the spheres 90 toward the distal end of the cylinder 82 and the cylinder spring 92. Thus, pump 84 may be referred to as a single stroke spring return pump. The length of the cylinder 82 may also increase when the spheres are moved toward the distal end of the cylinder 82. Girth increase may also be achieved by moving fluid to an area between distensible and non-distensible walls, wherein the wall diameter is slightly oversized so that it can initially expand outwardly until it reaches its fully expanded diameter. At that point, the cylinder can no longer expand outwardly and the distensible wall can be driven down around the spheres, thereby locking them in place. In order to release the spheres 90 and return the cylinder 82 to its more flexible state, the pump 84 is "released" so that the bias of the spring 94 allows fluid to move through the tube 86 toward the pump 84.

In this embodiment of the invention, it is possible for a single action by the user (i.e., activating the pump 84 with a single motion) to change the cylinder 82 from a relatively flexible state to a more rigid state. The volume of fluid needed in the system to cause this activation is relatively small.

Figure 4:
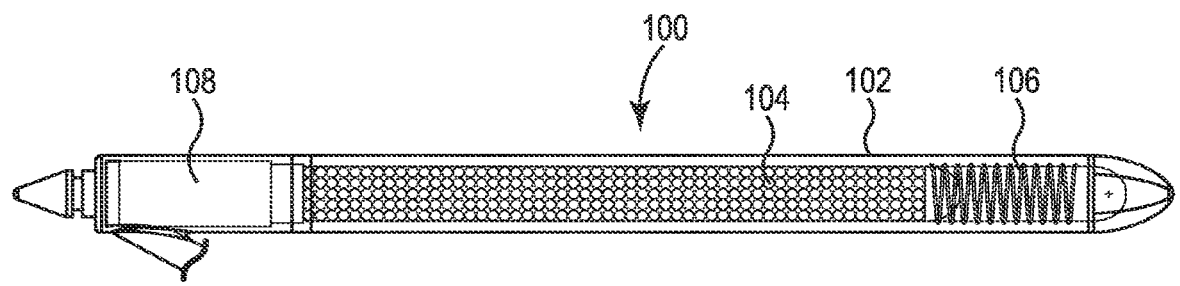
FIG. 4 is a front, partial cross-sectional view of an embodiment of a penile prosthesis system of the invention.

FIG. 4 illustrates another embodiment of a penile prosthesis system 100 that is similar to the system 80 of FIG. 3. In this embodiment, a hollow cylinder 102 also includes a spring 106 at its distal end and a plunger 108 at its proximal end, and contains a relatively large number of small spheres 104 and/or members having different shapes. The operation of this system 100 is generally similar to that of system 80, wherein the material that surrounds the spheres 104 within the cylinder 102 is distensible and can be driven down around the spheres 104 to "lock" them with minimal fluid volume transfer and low pressure by having it paired with a non-distensible outer member.

In aspects of the invention described herein, the penile prosthesis systems can alternatively or additionally include an integrated inflation system for transferring fluid to the cylinders. Such a system may include an electronic pump with remote activation thereof. For example, the system can include a piezoelectric pump for drawing fluid from a reservoir and moving the fluid to the cylinder(s). The piezoelectric pump can be wirelessly activated to control the inflation and/or deflation of the cylinder(s), and can include an actuator powered by an inductor coil integrated into the inflatable cylinder to allow for wireless control of the inflation and deflation of the cylinder(s). An example of such an electrical system is described in Applicant's co-pending U.S. Patent Application Publication No. 2013/0190559, the entire contents of which are incorporated herein by reference. For another example, the systems may include an electric pump, an implant controller, and an implantable power supply that provides power to the pump, such as is described in Applicant's co-pending U.S. Patent Application Publication No. 2014/0051920, the entire contents of which are incorporated herein by reference.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A penile prosthesis system comprising:
    at least one cylinder including:
        an inner member having an inner wall;
        an elongated inner opening defined by the inner wall;
        a cylinder spring positioned within the inner opening and adjacent to a distal end of the inner opening;
        an activation plunger positioned within a proximal end of the inner opening;
        an outer member surrounding the inner member; and
        a plurality of discrete members disposed within the inner opening between the cylinder spring and the plunger, the plurality of discrete members having a size approximately the same as a width dimension of the inner opening;
    a fluid disposed between the inner member and the outer member;
    a pump including at least one of a spring and an electronic pump; and
    a tube connected to and extending from the at least one cylinder and the pump,
    wherein the tube is configured for transferring the fluid to or from the at least one cylinder upon activation of the pump.

2. The penile prosthesis of claim 1, wherein the plurality of discrete members comprises a plurality of spherical members.

3. The penile prosthesis of claim 2, wherein the plurality of spherical members comprise at least one spherical member having a different size from the other spherical members.

4. The penile prosthesis of claim 1, further comprising a distensible material within the inner opening of the at least one cylinder.

5. The penile prosthesis of claim 1, wherein the plurality of discrete members comprise members having multiple sizes and shapes.

6. The penile prosthesis of claim 1, wherein the outer member is non-distensible.

7. The penile prosthesis of claim 1, wherein the inner member is distensible.

8. A penile prosthesis system comprising:
    at least one cylinder including:
        an inner member having an inner wall;
        an elongated inner opening defined by the inner wall;
        a cylinder spring positioned within the inner opening and adjacent to a distal end of the inner opening;
        an activation plunger positioned within a proximal end of the inner opening;
        an outer member surrounding the inner member; and
        a plurality of discrete members disposed within the inner opening between the cylinder spring and the plunger, each discrete member being adjacent to the inner wall of the at least one cylinder;
    a fluid disposed between the inner member and the outer member;
    a pump including at least one of a spring and an electronic pump; and
    a tube connected to and extending from the at least one cylinder and the pump,
    wherein the tube is configured for transferring the fluid to or from the at least one cylinder upon activation of the pump.

9. The penile prosthesis of claim 8, wherein the outer member is non-distensible.

10. The penile prosthesis of claim 8, wherein the inner member is distensible.

11. A penile prosthesis system comprising:
    at least one cylinder defining an inner opening, an outer member, an inner member disposed within the outer member, a cylinder spring positioned within the cylinder adjacent to a distal end of the inner opening, an activation plunger positioned within a proximal end of the inner opening, and a plurality of discrete members within the inner opening between the cylinder spring and the plunger;
    a fluid disposed between the inner member and the outer member;
    a pump; and
    a tube connected to and extending between the cylinder and the pump, wherein the tube is configured for transferring the fluid upon activation of the pump.

12. The penile prosthesis of claim 11, wherein the plurality of discrete members include a plurality of spherical members.

13. The penile prosthesis of claim 12, wherein the plurality of spherical members comprise at least one spherical member having a different size from the other spherical members.

14. The penile prosthesis of claim 11, wherein the plurality of discrete members include members having multiple sizes and shapes.

15. The penile prosthesis of claim 11, wherein the outer member is non-distensible.

16. The penile prosthesis of claim 11, wherein the inner member is distensible.

* * * * *